(12) United States Patent
Curtis

(10) Patent No.: US 7,187,455 B2
(45) Date of Patent: *Mar. 6, 2007

(54) PHOTOMETRIC CALIBRATION OF LIQUID VOLUMES

(75) Inventor: Richard H. Curtis, Gorham, ME (US)

(73) Assignee: Artel, Inc., Westbrook, ME (US)

( * ) Notice: Subject to any disclaimer, the term of this patent is extended or adjusted under 35 U.S.C. 154(b) by 185 days.

This patent is subject to a terminal disclaimer.

(21) Appl. No.: 10/827,611

(22) Filed: Apr. 19, 2004

(65) Prior Publication Data

US 2004/0246501 A1  Dec. 9, 2004

Related U.S. Application Data

(63) Continuation of application No. 10/021,112, filed on Dec. 12, 2001, now Pat. No. 6,741,365.

(51) Int. Cl.
*G01B 11/22* (2006.01)

(52) U.S. Cl. ........................ 356/627; 356/436

(58) Field of Classification Search ................ 356/627, 356/243.1, 243.2, 246, 320, 326, 435, 436; 250/577; 422/922; 436/164; 73/1.73, 1.74, 73/149, 290

See application file for complete search history.

(56) References Cited

U.S. PATENT DOCUMENTS

| 4,354,376 | A | 10/1982 | Greenfield et al. |
| 5,244,813 | A | 9/1993 | Walt et al. |
| 5,258,308 | A | 11/1993 | Freeman et al. |
| 5,298,978 | A | 3/1994 | Curtis et al. |
| 5,492,673 | A | 2/1996 | Curtis et al. |
| 5,766,875 | A | 6/1998 | Hafeman et al. |
| 5,959,738 | A | 9/1999 | Hafeman et al. |
| 5,963,318 | A | 10/1999 | Held |
| 6,188,476 | B1 | 2/2001 | Hafeman et al. |
| 6,320,662 | B1 | 11/2001 | Hafeman et al. |
| 6,339,472 | B1 | 1/2002 | Hafeman et al. |
| 6,741,365 | B2 * | 5/2004 | Curtis ........................ 356/627 |
| 2002/0149772 | A1 | 10/2002 | Halg |

* cited by examiner

*Primary Examiner*—Layla G. Lauchman
*Assistant Examiner*—Juan Valentin, II
(74) *Attorney, Agent, or Firm*—Verrill Dana, LLP; Chris A. Caseiro; Brian J. Libby

(57) ABSTRACT

A method and apparatus for measuring and calibrating the measurement of small volumes of liquids. The small volumes of liquid are typically dispensed from liquid delivery devices, the delivery device often having multiple channels to analyze many samples at once. The liquid samples are delivered to one or more cells, typically in a multi-well plate, and positioned in a spectrophotometer for determining an absorbance of a chromophore in the liquid sample. Based upon an absorbance measurement and the concentration of the chromophore, a path length of the liquid sample is determined, from which a volume of the sample may be calculated. The method and apparatus provide various means for correcting for differences in the dimensions and/or other factors causing a non-linear deviation from the Beer-Lambert law. A system or kit may be provided including sets of sample solutions of varying dilution ranges for calibrating different liquid volumes. The kit may further include software code for storing and analyzing the various sample solutions.

27 Claims, 4 Drawing Sheets

PHOTOMETRIC CALIBRATION OF LIQUID VOLUMES

CROSS REFERENCE TO RELATED APPLICATION

The present application is a continuation of, and claims the priority benefit of, U.S. patent application Ser. No. 10/021,112, filed Dec. 12, 2001, entitled "PHOTOMETRIC CALIBRATION OF LIQUID VOLUMES" now U.S. Pat. No. 6,741,365 issued May 25, 2004, of the same named inventor and assigned to a common assignee. The entire contents of that prior application are incorporated herein by reference.

FIELD OF THE INVENTION

The present invention relates to a method and apparatus for measuring and calibrating the measurement of a liquid volume. The liquid volume can be delivered from one or a multiplicity of orifices or tips simultaneously or sequentially. Also described are a test methodology, an algorithm for calculating results, a system of liquid reagents, a method of calibrating a photometric reader, and software that coordinates, controls and carries out these activities.

BACKGROUND OF THE INVENTION

Many analysis methods used in biology, chemistry, biotechnology, pharmaceutical and other research laboratories require accurate measurement and/or calibration of small volumes of liquids. These small volumes can range from nanoliters to milliliters. In one application, small volumes of liquid are dispensed from liquid delivery devices comprising a single delivery orifice or multiple orifices configured to deliver liquid simultaneously or sequentially. Specific examples include handheld multichannel pipettes, configured to deliver 8 or 12 channels at a time, and automated delivery equipment configured to deliver 96 or 384 channels at one time. In other applications, there is measured a precise amount of liquid contained by a small volume vessel.

For liquid delivery devices, the delivery must be both accurate and precise. At any given time the delivery device may not be functioning within the requirements of the process or the specifications of the manufacturer. For this reason it is necessarily to periodically calibrate the delivery equipment to ensure its correct operation and the integrity of the analysis.

Multi-channel delivery devices are typically used to expedite the analysis or processing of many samples at once, or to analyze one sample for many different attributes at once. In order to assure the integrity of the multi-analysis process, the equipment must be functioning correctly at the time of the analysis. Existing calibration methods have various limitations that prevent timely, convenient, accurate and/or precise calibration activities, thus bringing into question the results of the analysis. Several of these existing calibration methods are described below.

In the gravimetric method, a liquid volume is determined by weight. After initially weighing a receiving tube, the liquid volume is delivered into the tube. The tube is reweighed and the weight gain of the filled tube leads to calculation of the liquid volume, after correction for the density of the fluid, the loss of fluid due to evaporation during the procedure, and the buoyancy of air. The gravimetric method, however, is extremely time consuming, particularly for calibrating multiple liquid volumes as done with multi-channel liquid delivery devices where hundreds of liquid deliveries occur simultaneously. In the case of small delivery volumes, the errors introduced into the weighing by vibration, draft, static electricity, and/or evaporation cause this method to be of questionable utility or validity.

The gravimetric method can be applied to multiple volumes by the use of microtiter plates as the receiving vessel. Microtiter plates are rectangular molded plastic plates having a multiplicity of small cavities or wells to receive the liquid being delivered. Exemplary microtiter plates have 96 or 384 wells. In this method, the amount of liquid delivered to the wells is not measured individually. A complete microtiter plate is weighed without the liquid, the wells are filled and the plate is then re-weighed. The resulting weight gain is converted to liquid volume by accounting for liquid density, evaporation, and air buoyancy. The total volume contained by the microtiter plate is divided by the number of filled wells. Thus, this procedure measures the average liquid delivery volume. This method is disadvantageous for calibrating multiple-orifice delivery devices because no information is provided on the amount delivered from an individual orifice.

In the photometric method, a sample holder having a transparent bottom surface receives the liquid volume to be determined. A beam of light passes through the bottom surface and the liquid and eventually to a detector. The amount of light absorbed, i.e. the absorbance, provides information on the depth of the liquid and thus, the volume, taking into account certain properties of components of the liquid, such as concentration and molar absorptivity (or extinction coefficient). For example, if the liquid volume contains a dye capable of absorbing the light, the amount of liquid present can be estimated by measuring the amount of light absorbed as it passes through the well. The more liquid dispensed into a given well, the deeper the column of liquid, and the more light absorbed. Spectrophotometers for measuring the absorbance of the liquid by this technique are well known and are commonly called microplate readers or microtiter plate readers, where the photometric method is used with specially constructed microtiter plates. In the current implementation, however, the photometric method fails to provide an adequate level of accuracy for many uses.

Another means of calibration is to dispense liquid that contains a diluted amount of a fluorophore, such as fluorescein, into a microtiter plate. A specialized plate reader measures the amount of fluorescence coming from each well of the microtiter plate. As with the photometric method, this method is generally not sufficiently accurate to satisfy the needs of many users. There are no stable or recognized standards for calibrating the sensitivity of such fluorescent readers, making it impossible for this method to be used alone to provide a quantitative result traceable to a national standard (e.g., as set by a recognized standards organization, such as ASTM).

SUMMARY OF THE INVENTION

In select embodiments, the present invention provides an easy to use, fast, accurate and precise method and apparatus for the calibration of liquid delivery devices. It provides results that are traceable to (within) national standards. The method is particularly useful for the calibration of small liquid volumes, such as in multichannel delivery devices. It allows semi-skilled laboratory technicians to practically and easily calibrate such equipment and on a schedule that provides for data integrity.

According to one aspect of the invention, a method is provided for calibrating a liquid volume. The method includes providing a sample solution including a first chromophore having an absorbance maximum at a first wavelength and a second chromophore having an absorbance maximum at a second wavelength. The difference between the first and second absorbance maxima is at least about 100 nm. The sample solution is exposed to electromagnetic radiation, and the absorbance by each chromophore is measured. A blank solution is also exposed to electromagnetic radiation, the blank solution being free of the first chromophore and including the second chromophore in a concentration equal to that in the sample solution. The absorbance of the blank solution is measured. A volume of the sample solution is determined based upon the measured absorbances of the blank solution and the sample solution.

According to another aspect of the invention, a liquid volume calibration system is provided including a spectrophotometer for emitting and detecting electromagnetic radiation. A multi-well plate is provided for containing a plurality of sample solutions and for exposing the solutions to the electromagnetic radiation. Each of the plurality of sample solutions includes a first chromophore having an absorbance maximum at a first wavelength and a second chromophore having an absorbance maximum at a second wavelength, the difference between the first and second absorbance maxima being at least 100 nm, and each sample solution having a unique concentration of at least the first chromophore. A separate blank solution is provided free of the first chromophore and including the second chromophore in a concentration equal to that in the sample solution.

According to another aspect of the invention, a system is provided including the plurality of sample solutions described in the immediately preceding paragraph, and a multi-well plate for containing the plurality of sample solutions and for exposing the solutions to electromagnetic radiation. Each well of the multi-well plate has a path length dimension provided to a level of accuracy of no more than 0.5%. A separate blank solution is provided free of the first chromophore and including the second chromophore.

According to another aspect of the invention, a system is provided including a calibration plate for calibrating a first spectrophotometer with a second spectrophotometer, the calibration plate having multiple cells containing a first set of calibration solutions. The system further includes a second set of sample solutions each including a first chromophore having an absorbance maximum at a first wavelength and a second chromophore having an absorbance maximum at a second wavelength, the difference between the first and second absorbance maxima being at least one 100 nm. A multi-well plate is provided for containing a plurality of the sample solutions for use in the first spectrophotometer. A separate blank solution is provided free of the first chromophore and including the second chromophore in a concentration equal to that in the sample solution.

According to another aspect, a method is provided for determining a liquid volume. The method includes a step of providing a multi-well plate, providing a sample solution having an unknown volume and contained in a well of the multi-well plate, and maintaining a contact angle from about 80 to 100 degrees between a meniscus of the sample solution and the well, the contact angle being determined by concentrations of one or more of a chromophore, a salt, and a buffer in the sample solution. The sample solution is exposed to electromagnetic radiation and the absorbance of the chromophore is measured. The volume of the solution is determined based on the measured absorbance and the concentration of the chromophore.

In yet another embodiment, a computer-executable software code is stored on a computer-readable medium, the code including code for calculating a volume of a liquid sample solution based upon a photometric reading of absorbance, a concentration of a chromophore in the sample solution, a path length dimension of a sample holder in which the reading is made, and a quantification of a non-linearity from the Beer-Lambert law of the reading.

DETAILED DESCRIPTION

One aspect of the present invention provides a method of calibrating a liquid volume. The calibration uses a sample solution having a first and a second chromophore, and a blank or reference solution having only the second chromophore, i.e. the blank is free of the first chromophore. The concentration of the second chromophore in the sample and blank solutions is the same. This allows the blank solution to serve as the diluent. If the diluent is added to the sample; preferably the amount to be added is calculated based on readings at two wavelengths.

Prior art photometric calibration techniques have provided only one chromophore in either the reference or the sample solution, and a sample holder not of an idealized geometry. This results in two unknowns—amounts of sample and amount of diluent, but only one piece of data, i.e. the absorbance. In contrast, the provision of two chromophores in the sample solution gives two reference points for the calibration, i.e. two absorbance readings at two wavelengths, providing sufficient information to calculate the volume of both the diluent and the sample solution. This aspect of the invention thus leads to higher accuracy and precision, as described in greater detail below.

In one embodiment, the calibration technique is applicable with only one sample solution where the chromophores obey the Beer-Lambert law. According to this law, the relationship between the absorbance of light A passing through a liquid and the path length l is shown in eq. (1):

$$A = \epsilon c l \quad (1)$$

where $\epsilon$ is the molar absorptivity (sometimes also called the extinction coefficient) of the chromophore, and c is its concentration in moles per liter. The latter two quantities are predetermined in the manufacture of the reagent. If their values are known, and the absorbance A of a solution has been measured in a photometric instrument, then the path length l can be determined by calculation.

Figure 1:
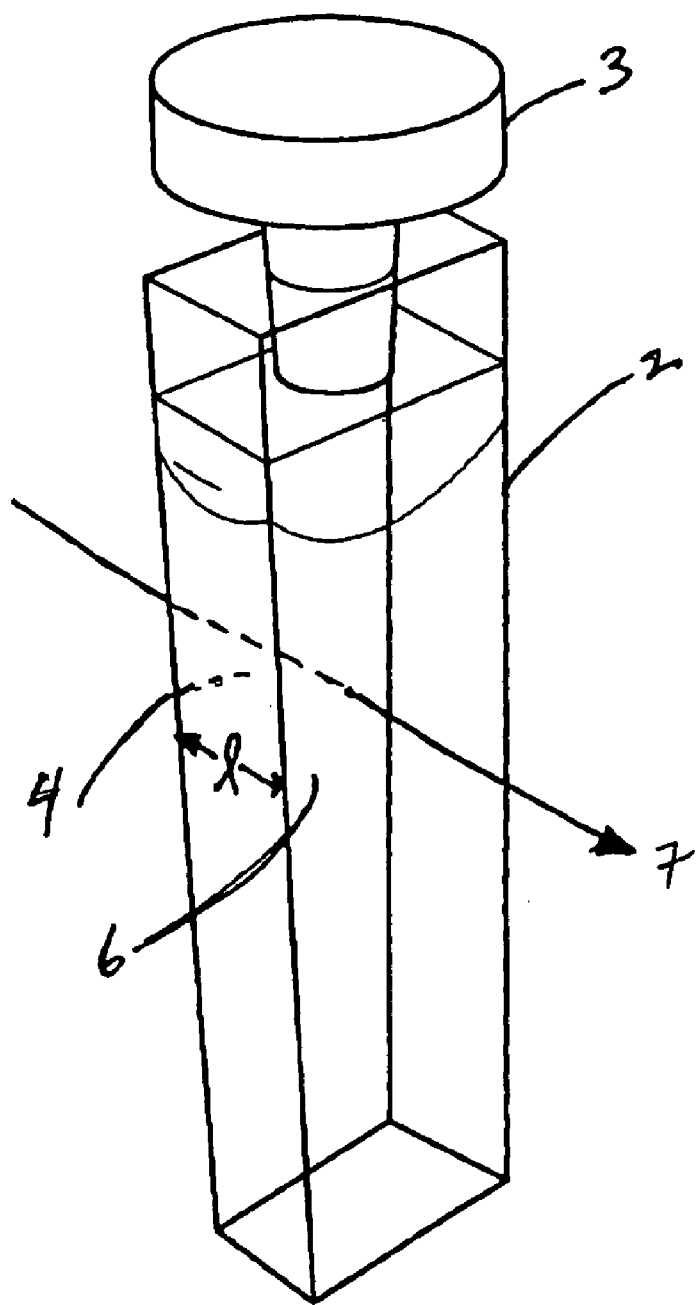
FIG. 1 is a schematic diagram of one embodiment of a cell or cuvette having opposed parallel transparent walls that provide a fixed path length l.

The reference and sample solutions are exposed to electromagnetic radiation, preferably in the ultraviolet-visible light region of the electromagnetic spectrum. In one embodiment, exposure to electromagnetic radiation occurs via a horizontal beam. FIG. 1 shows an example of a commercially-available cell or cuvette 2, for holding the liquid solution and having an open top end closed by a cap 3. Cap 3 minimizes evaporation of the solution in the cuvette and prevents spillage. Cuvette 2 includes opposing parallel transparent walls 4 and 6, allowing radiation to penetrate through the transparent walls 4, 6 and the liquid therebetween to a detector. In a typical photometric experiment, cuvette 2 is positioned vertically and a solution in cuvette 2 is exposed to a horizontal beam, i.e. perpendicular to the faces of walls 4 and 6, as shown in the direction of arrow 7. The path length l is equal to the distance between the inner surfaces of the transparent walls 4 and 6. In an alternative embodiment, exposure to electromagnetic radiation occurs via a vertical beam, where the cuvette is positioned horizontally and a vertical beam is perpendicular to and penetrates the opposed transparent walls.

Figure 2:
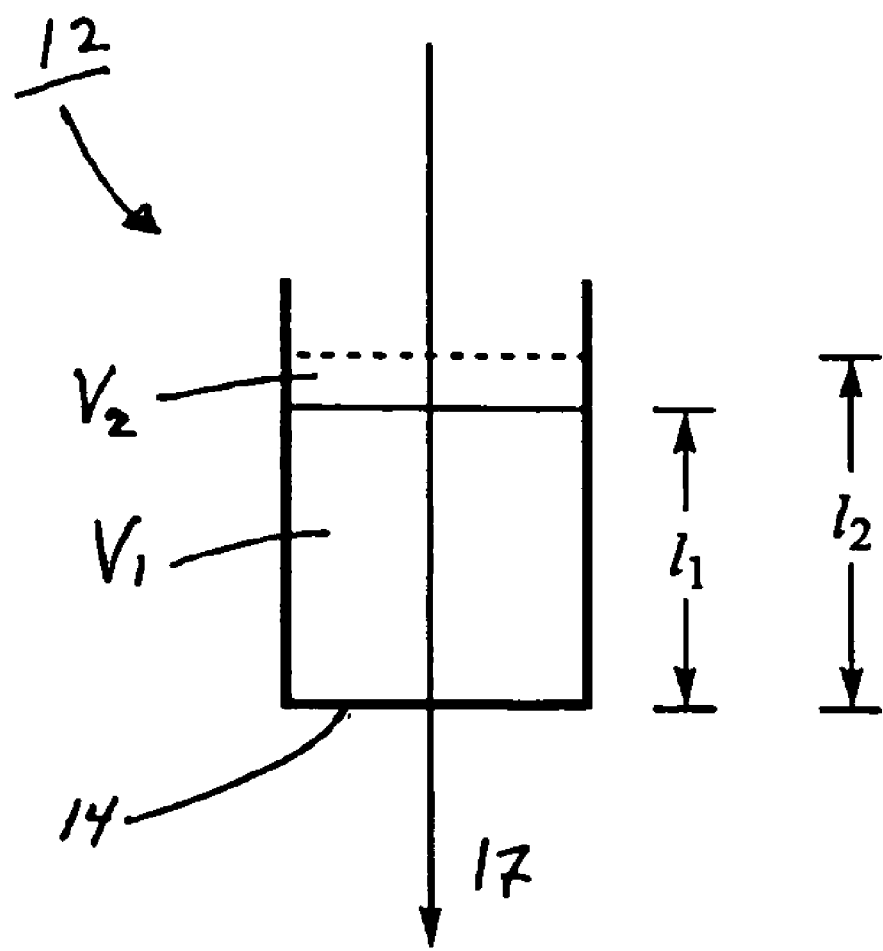
FIG. 2 is a schematic cross-section of another embodiment of a cell with a transparent bottom designed for vertical beam spectroscopy and accommodating varying amounts of liquid volumes to provide a variable path length l.

FIG. 1 shows a cell with a fixed solution path length l. In another embodiment, a cell allows a variable volume of the solution for use in vertical beam photometry. FIG. 2 is a schematic representation of such a variable volume cell 12 having at least a transparent floor 14, and optionally an opposing ceiling that is also transparent (not shown). A vertical beam of light perpendicular to floor 14 and traveling in the direction of arrow 17 penetrates the solution in cell 12. A depth of liquid in cell 12 is also the path length of light through the solution. Adding, for example, more sample solution in the cell causes the solution volume to rise from $V_1$ (solid line) to $V_2$ (dotted line), producing a corresponding change in solution path length from $l_1$ to $l_2$. The more liquid dispensed into a given cell, the deeper the column of liquid, and the more light absorbed by the solution. Again, from the measured absorbances, the path length l can be calculated and the volume determined.

For increased accuracy, the measured maximum absorbances should be attributable to only one chromophore, i.e. the absorbance maximum of a first chromophore does not overlap with that of a second chromophore. Preferably, the absorbance maxima of the first and second chromophores occur at first and second wavelengths, respectively, such that the respective absorbance maxima minimally overlap with each other. In one embodiment, the absorbance maxima of the first and second chromophores differ by at least 100 nm. If even greater accuracy is desired, preferably the absorbance of the second chromophore at the first wavelength is no more than about 10% its absorbance at the second wavelength, preferably no more than about 5%, and even more preferably no more than about 2% its absorbance at the second wavelength. This provides minimal overlap of the second chromophore with the absorbance maximum of the first chromophore at the first wavelength.

FIG. 2 shows an idealized solution volume where the top solution surface is perfectly flat. Here, calculation of the liquid volume is trivial. In reality, however, particularly in a small cell such as a microtiter plate well, the liquid typically interacts with the material of the cell wall causing the liquid surface or meniscus to be non planar. This is true for commonly-available microtiter plates and chromophore materials.

Figure 3A:
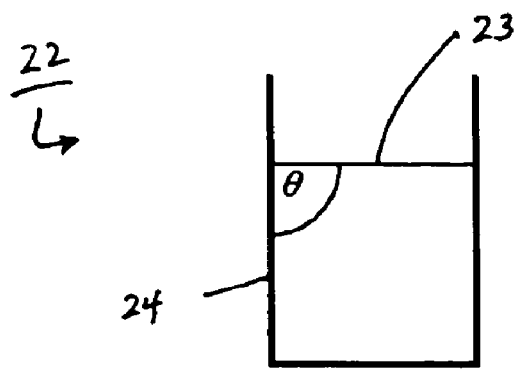
FIG. 3A is a schematic cross-section of a solution in a cell displaying an idealized flat meniscus to provide a 90 degree contact angle $\theta$.
Figure 3B:
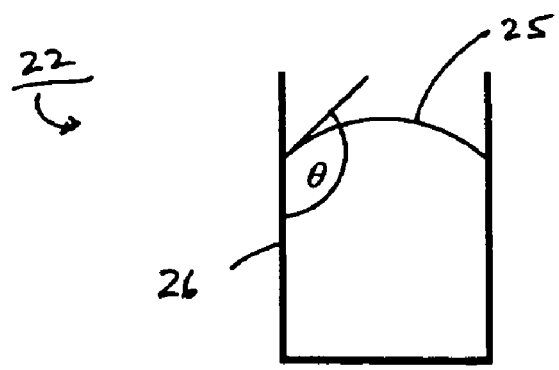
FIG. 3B is a schematic cross-section of a solution in a cell displaying a convex meniscus to provide a contact angle $\theta$ in the solution of greater than 90 degrees.
Figure 3C:
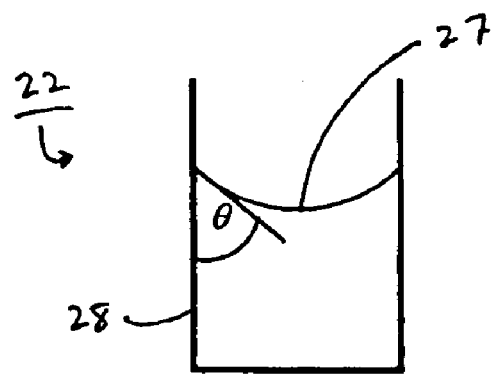
FIG. 3C is a schematic cross-section of a solution in a cell displaying a concave meniscus to provide a contact angle $\theta$ in the solution of less than 90 degrees.

FIG. 3 shows three possible shapes of the meniscus. FIG. 3A reproduces the idealized flat meniscus of FIG. 2, where a contact angle θ in the solution between meniscus 23 and sidewall 24 of cell 22 is 90 degrees. If, however, the plate is made of, for example untreated polystyrene (as is common), and the liquid behaves similarly to water, then the meniscus will be convex. This convex meniscus is schematically shown in FIG. 3B, where a contact angle θ in the solution between convex meniscus 25 and sidewall 26 has a value greater than 90 degrees. In another common situation, if the surface of cell 22 has been treated to be hydrophilic, and the liquid behaves similarly to water, then the meniscus will be concave. FIG. 3C schematically shows a contact angle θ in the solution between a concave meniscus 27 and sidewall 28 having a value of less than 90 degrees. In the case of a concave or convex meniscus, the path length of a vertical beam of light traversing through the center of the well is dependent on the shape of the meniscus. For a given volume of liquid in the well, a convex meniscus will produce a longer path length and a concave meniscus will produce a shorter path length. Thus, a calculation of the amount of liquid in the well based on a measurement of this path length by optical means will give different results in the two cases. The error introduced by deviation of the meniscus from a flat shape can be quite severe, for example deviating by a value of up to 20%.

Accordingly, in one embodiment of the invention, the calibration method comprises maintaining a contact angle in the solution from about 80 degrees to about 100 degrees. Maintaining the contact angle can be achieved for example by selecting the cell materials and solution materials and correlating them with at least one component in the solution.

The solution components can affect the contact angle in various ways. Many dyes in aqueous solution cause the contact angle to be substantially less than 90 degrees. Preferably, a dye is used that causes only a minimal depression of the contact angle. Exemplary dyes include Ponceau S and Amaranth. When a salt such as sodium chloride is added to a dye solution, the contact angle increases. Preferably, a sufficient amount of salt is added to produce the desired contact angle. The choice of buffer, used for maintaining solution pH, is also important. Preferably a buffer is chosen that causes only a minimal deviation of the contact angle from 90 degrees. One class of such buffers is phthalate buffer (e.g. 0.02 M; pH 6), which only causes a minimal deviation of the contact angle from 90 degrees, while still stabilizing pH.

In one embodiment, the microtiter plates themselves are chosen to comprise a material compatible with the solution components to produce the desired contact angle. For example, the microtiter plate can comprise a material such as polystyrene.

In another embodiment, a buffer is chosen to stabilize the absorbance of the sample solutions as they are exposed to air or other gaseous environment.

In another embodiment, greater accuracy is obtained by determining the actual shape of the cell and accurately measuring at least one dimension. For example, in a multi-well microtiter plate, each well is assumed to have a cylindrical shape where a cross-section of each well is schematically represented by cell 12 in FIG. 2. Thus, in calculating the volume, prior art methods assume the dimensions of a perfect cylinder. Each well, however, is actually a truncated cone, because the microtiter plates are formed from plastic by injection molding. In this process, plastic is melted and injected into a molded cavity of the desired shape and dimensions. Once the plastic has cooled, the cavity is opened and the part removed. In order to enable the hardened part to be removed without distortion or marring, each feature or indentation of any depth must have a taper or "draft" angle to allow undistorted removal. Thus, in the case of microtiter plates, the wells are tapered to the extent of several degrees, with the larger area being toward the open end of the well. An erroneous assumption that the well is a perfect cylinder can lead to an error in computed volume of up to 5 percent.

In one embodiment, it is not assumed that the wells have a perfect dimension. In the example of a cylindrical cell or well, when making calculations of liquid volume in the well, the degree of taper or draft in the well is quantified. In another embodiment, the diameter of the well is measured. In yet another embodiment, both the degree of taper and diameter are measured. Preferably, these measurements are made to a level of accuracy of no more than 0.5%, preferably no more than 0.2% and even more preferably no more than 0.1%. For example, when used with commercially available multi-well microtiter plates, the method of the present invention treats the actual shape of the well as a truncated cone of diameter and taper given by the measured dimensions. The volume of a well of this shape filled to a depth l is given by:

$$V_T = \pi l \frac{\phi^2}{4} + \pi \phi l^2 \frac{\tan(\gamma)}{2} + \pi l^3 \frac{\tan^2(\gamma)}{3} \qquad (2)$$

where $\phi$ is the diameter of the well at the bottom, and $\gamma$ is the half angle of the taper.

In another embodiment, each individual well in a multi-well plate is accurately measured using a method traceable to national standards. Another assumption made in prior art calibration methods is that each well in the plate is the same dimension from one plate to the next, or from one group or lot of plates to the next. In actuality, there is a variability in the dimensions of a molded plastic part depending on the exact conditions of molding, e.g. temperatures of the mold and the molten plastic as it enters the mold, the cooling time of the part in the mold before it is ejected, the moisture content of the plastic raw material before molding, as well as on the dimensions of the mold. This variability reduces the ability to reproduce well dimensions to a high level of accuracy. Typical manufacturer dimensional specifications for a 96 well plate provide a diameter of all wells within 1% of the nominal diameter. A 1% error in well diameter, however, leads to a 2% error in the computed delivery volume. In one embodiment, the method of the invention, each well of a multi-well plate is measured in at least one dimension to a level of accuracy of no more than 0.5%, preferably no more than 0.2%, and more preferably no more than 0.1%. In this way, error due to plate-to-plate variability is substantially reduced.

Certain solutions do not obey the Beer-Lambert law because of the solution concentration, the chromophore properties, or for other reasons, resulting in a deviation from the Beer-Lambert law by several percent. For some chromophores, only select concentration ranges of the chromophore will result in accurate absorption readings. In such a situation, the measured absorbances of several samples of varying dilutions are required for the calculation. In one embodiment, adherence to the Beer-Lambert law is not assumed and a number of dilutions of the sample solution are prepared, encompassing the range of dilutions that are expected when the system is put into use. In one embodiment, the sample solution is one of a plurality of solutions where each sample solution presents a unique concentration of at least the first chromophore. A ratio of absorbance data is taken of the plurality of samples at the two wavelengths. The ratio of absorbance data at the two wavelengths is then plotted vs. the ratio of dilution of the sample solution. The data may be fit to a cubic equation with three coefficients determined by a least squares regression analysis. This calculation is discussed in further detail below.

Where it is necessary to dilute the sample solution to obtain a good photometric reading, it is advantageous to have the blank solution include the second chromophore in a concentration equal to that in the sample solution, as the blank solution can then also act as a diluent for the sample solution. Diluting the sample solution with the blank solution results in decreasing the concentration of the first chromophore, while the second chromophore concentration remains constant. Mixing the blank solution with the sample solution to a suitable homogeneity serves to increase the volume to the point that an accurate photometric reading can be made.

At least some of the corrections discussed overcome another assumption commonly made that can lead to errors, i.e. if diluent is added to the wells in addition to the dye-containing sample, it will not affect the results of the calibration. However, when calibrating small liquid volumes, the liquid does not necessarily spread out and cover the bottom of the well uniformly; rather, it tends to ball up and remain at the edge of the well at the bottom making a meaningful photometric measurement impossible. A typical practice is to introduce additional liquid to act as a diluent, resulting in enough volume to reliably cover the bottom of the well. However, because the wells are in the form of truncated cones, there is a non-linear relationship between the amount of diluent added and the absorbance reading. Additionally, the lack of adherence to the Beer-Lambert law results in a further deviation from the assumed independence of the volume from the diluent added. Also, the diluent is generally added using a delivery device whose calibration may be as uncertain as that of the device being tested. Thus, the problem of calibrating one device has not been solved, but rather transferred to the problem of calibrating another device.

Another incorrect assumption commonly made is that the absorbance of the dye is the same when contained in a closed vessel, such as a cuvette, as it is when exposed to the environment (e.g., air) in a microtiter plate. Most organic dyes are sensitive to changes in pH, and will change absorbance when the solution absorbs carbon dioxide from the air. Thus, in another embodiment, the method comprises selecting a chromophore exhibiting minimal absorbance changes when exposed to an intended environment of use, e.g., air.

The temperature of the solution can measurably affect the absorbance of the chromophore. Typically, organic dyes change their absorbances as the temperature changes. In yet another embodiment, the method comprises selecting a chromophore exhibiting a reduced temperature dependence of absorbance. Preferably, the temperature dependence is less than 0.05% per degree centigrade. Exemplary chromophores meeting this requirement include Amaranth and Ponceau S. If even greater accuracy is required, the temperature of the reagents at the time of use is measured, and a correction is applied in the calculation algorithm when the results are calculated.

Another aspect of the invention provides a system or kit for calibrating a liquid volume. The kit comprises several components that allow a user to calibrate a desired liquid volume quickly and in a facile manner. For example the system can comprise any one or all of the components previously described. In one embodiment, the kit includes a plurality of sample solutions, each sample solution comprising a first chromophore providing an absorbance maximum at a first wavelength and a second chromophore providing an absorbance maximum at a second wavelength, the difference between the first and second absorbance maxima being at least 100 nm, and each sample solution having a unique concentration of at least the first chromophore. The kit can comprise a set of sample solutions with dilutions for a particular, desired volume range. For example, if a user wants to calibrate a liquid volume in the nanoliter range, the kit can contain instructions to use a certain set of sample solutions for that range. If a user wants to calibrate a liquid volume in the microliter range, the user will turn to a different set of sample solutions, as instructed. Alternatively, the kit can contain concentrated sample solutions and a diluent having the same components as the blank solution, with instructions for the user to prepare the appropriate dilutions for the volume being used. Preferably all of the sample solutions contain the same concentration of the second chromophore.

The kit can also include a reference or blank solution free of the first chromophore and including the second chromophore. Preferably, the concentration of the second chromophore is the same as that in the sample solutions.

The kit can also include an accurately measured sample holder or, for multiple calibrations, a multi-well microtiter plate. In accordance with an embodiment described previously, a precise mapping of the actual shape is taken into account and an accurate measurement of at least one dimension, such as the diameter and/or degree of taper, is performed, preferably to a level of accuracy of no more than about 0.5%, preferably no more than about 0.2% and even more preferably no more than about 0.1%. Preferably, the physical dimensions of the wells in these plates are measured using a method traceable to national standards.

The kit may also include an algorithm implemented in hardware or in computer-executable software stored on a computer-readable media, e.g., on a floppy disk, RAM, ROM, a hard disk, optical medium, etc. It is possible to express the same algorithm in many different computer languages, or even to build it into hardware by connecting the appropriate registers and logic gates. The computer program may act as a user interface, allowing the user to input data or otherwise facilitate the transfer of data for later use in the calculation of results. The program may also prompt the user for necessary actions and provide results in visual form, as computer files and/or in printed form. The computer program may also provide an interface to other computer programs, such as may be operating the spectrophotometer or plate reader, wherein the program may acquire data from the plate reader.

The algorithm calculates results based on inputs from the user, the results of the photometric readings, information provided about the kit components and calibration plate, and/or from other automated or manual sources. The software used to implement the algorithm can include data on the various kit components, accept as input data absorbance readings, and use this data in the calculation of the liquid volume. In one embodiment, the various kit components are encoded with a bar code that can be scanned or inputted into the computer and read by the software for the calculation. Such encoded information can include any one or a combination of the type of chromophore in the sample and/or blank solutions or the concentration of the chromophore in the sample and/or blank solutions. Individual cells or individual wells of microtiter plates can be encoded with the actual diameter and degree of taper for a given well. These dimensions may be recorded on a bar code that is printed and affixed to the plate itself, or these dimensions can be provided in the kit instructions and manually inputted by the user, or by any other input method known to those of ordinary skill in the art.

When a user begins the calibration process, the user can scan the barcode or otherwise transfer the information into the computer for use by the calculation algorithm. At the time of use, this bar code is read, or the information is transferred to the calculation algorithm by other means, and the diameter and/or taper information is used in the calculation.

Other encoded information may include specific properties of the sample and blank solutions, particularly those properties that quantify the extent of non-linearity from the Beer-Lambert law. In one embodiment, these properties can be calculated by a manufacturer and provided to the user in the kit. In another embodiment, the kit can include instructions for a user to carry out the measurements and calculations necessary to obtain these properties.

In one embodiment for quantifying the extent of non-linearity from the Beer-Lambert law, a correction factor is calculated to rectify error inherent in the spectroscopic method. A cell or multi-well plate is weighed and then filled with a sample solution. The cell is weighed again and the difference in weight provides the sample solution weight. From the sample solution weight, a volume of the sample solution can be calculated. An absorbance of this same sample solution is taken, and from the Beer-Lambert law of equation (1), the path length and thus the volume can be calculated. By comparing this volume with that determined by the weighing method, a correction factor is calculated. This correction factor is provided to the user in the kit instructions, or encoded as a property of the particular sample solution.

As described previously, the blank solution includes the second chromophore only. Preferably, the blank solution includes an appropriate amount of a suitable buffer, such as a phthalate buffer. In one embodiment, the manufacturer performs this procedure to characterize the reagents at the time of manufacture. The results of these measurements can be transferred to a computer program via a bar code, or other known methods, and provided in the kit. The spectrophotometer is zeroed and an absorbance of the blank solution is measured over a range of wavelengths, to accurately determine the wavelength of the absorbance maximum. This range of wavelengths should include the first wavelength, $\lambda_1$, at which the first chromophore exhibits an absorbance maximum, and the second wavelength, $\lambda_2$, at which the second chromophore exhibits an absorbance maximum. In one embodiment, the absorbance of the blank solution is measured in the 400–800 nm range. The absorbance maximum of the blank is noted at wavelength value of $\lambda_2$, as the blank only contains the second chromophore. Preferably, the blank solution provides an absorbance at $\lambda_1$ having a value no greater than 10% the absorbance at $\lambda_2$, as discussed previously. This prevents significant inaccuracies in measuring the maximum absorbance of the first chromophore in the sample solution.

The following relationships can be obtained from the Beer-Lambert law:

$$A'_{b1} = \epsilon'_{b1} c'_b l' \text{ at } \lambda_1 \quad (3)$$

$$A'_{b3} = \epsilon'_{b3} c'_b l' \text{ at } \lambda_3 \quad (4)$$

If the manufacturer is carrying out this procedure for providing results to a customer or end user, the prime marks indicate that the data is being taken on the manufacturer's spectrophotometer, referred to herein as the "reference spectrophotometer." If the user is carrying out these procedures, the prime marks bear no significance and can be deleted. The subscript b refers to the blank solution being measured. The subscript "1" denotes the absorbance measurement at $\lambda_1$ and subscript "3" denotes the absorbance measurement at $\lambda_3$. The variable l' is the solution path length.

The kit comprises a set of sample solutions of varying dilution ranges for calibrating different liquid volumes. For example, the sample solutions can include a set of Range B sample solutions and Range C sample solutions, where Range B are useful for calibrating volumes in the range of 10 to 50 microliters, and Range C are useful for calibrating volumes in the range of 2 to 10 microliters. These ranges are exemplary only and those of ordinary skill in the art can determine other volume ranges for the sample solutions. The kit can include already prepared sets of sample solutions, preferably sealed to prevent evaporation.

Alternatively, the kit can contain concentrated sample solutions and a diluent having the same components as the blank solution, with instructions to the user for preparing the appropriate dilutions for the volume being used. The solution should be sufficiently diluted to allow the measured absorbance to come within the spectrophotometer range, typically A<2.5.

Dilutions are preferably made by weight, such as with a four-place balance. The dilution ratio $RD'_B$ is the volume of the sample solution divided by the sum of the volumes of the sample solution plus the blank solution:

$$RD'_B = \frac{V_B}{V_B + V_b} = \frac{w_B/\rho_B}{w_B/\rho_B + w_b/\rho_b} \quad (5)$$

where $\rho_B$ and $\rho_b$ denote the densities of the Range B and blank solutions respectively. For dilutions of Range C, the subscripts are changed to C in the various equations.

Preferably there are several dilutions for each sample solution, corresponding to the differing dilutions that occur when different volumes are calibrated.

These dilutions can be read in a fixed length cell in a reference spectrophotometer at two wavelengths. The absorbance spectrum of each of the sample solutions provides an absorbance maximum at the first wavelength, i.e. $\lambda_1$, which is the sum of two contributions: absorbance from the first chromophore having an absorbance maximum at $\lambda_1$ and a much smaller absorbance from the absorbance of the blank solution at $\lambda_1$. This sum is shown in eq. (6):

$$A'_{B1} = \epsilon'_{B1}(RD'_B c'_B)l' + \epsilon'_{b1} c'_b l' \quad (6)$$

where $c'_B$ is the concentration of dye in the undiluted Range B solution. Multiplying $c'_B$ by the dilution ratio $RD'_B$ gives the concentration of dye in the diluted solution. Note that $c'_b$, the concentration of chromophore b (e.g., copper ions) in this dilution, is the same as the concentration of chromophore b in the blank, since the blank solution has been used as the diluent both in creating the range solution and when diluting the range solution for reading in the reference spectrophotometer.

The Reagent Concentration Ratio (RCR) can be used to characterize the strength of the absorbance of the first chromophore in relation to the second chromophore. This ratio is provided in eq. (7):

$$RCR'_B \equiv \frac{\epsilon'_{B1} c'_B}{\epsilon'_{b3} c'_b} \quad (7)$$

Applying equations (3), (5) and (6) to equation (7) provides an RCR expressed in terms of measured quantities, as shown in eq. (8):

$$RCR'_B = \frac{A'_{B1} - A'_{b1}}{RD'_B A'_{b3}} \quad (8)$$

For a reagent system that does not obey the Beer-Lambert law perfectly (non-linear response), one value of RCR will not suffice for all dilutions of the sample solution. By measuring several dilutions, the deviation from linearity can be characterized and a correction factor applied. The different RCR values for different dilutions are labeled $RCR'_B(1)$, $RCR'_B(2)$, etc. If these RCR values are plotted against the dilution ratio $RD'_B$, the data fits well with a quadratic equation of the form:

$$RCR_B = RCR_B(0)[1 - a\ RD_B - b\ RD_B^2] \quad (9)$$

where $RCR_B(0)$, a and b are constants chosen to give a good fit to the test data. For the current lot of Range B, the constants are $RCR_B(0) = 27.0167$ $a = +0.14$ $b = -0.17 \quad (10)$ These three coefficients characterize the deviation from the Beer-Lambert law for this particular lot of reagent and are used in calculating results when the lot of reagent is used to calibrate a liquid delivery device. This information can also be encoded with the sample solutions provided in the kit, for input into the computer and used in the calculation of the liquid volume with the software provided. Preferably, the constants are reevaluated for each lot of reagent.

A user can perform the measurements and calculations necessary for obtaining the various correction factors previously described. Alternatively, a manufacturer can carry out these processes and provide the resulting correction factors to an end user in a kit. The end user immediately applies these correction factors in the calibration method without having to perform the initial measurements. It cannot be assumed, however, that for the same absorbent solution, the user's spectrophotometer will obtain the same results as those obtained from the manufacturer's spectrophotometer. For example, the manufacturer may have carried out the measurements via horizontal beam spectroscopy whereas the user calibrates the liquid volumes with vertical beam spectroscopy, i.e. with a plate reader. The design of the two photometers inherently provides differences in the measured absorbances. Plate readers are specialized to make readings of many samples in a short time through samples of short path length (typically ½ cm or less), whereas horizontal beam spectrophotometers are typically more oriented toward longer path length readings (meaning more highly collimated beams) and toward more exacting measurements. No commercially-available plate reader has as good specifications for any parameter as does even a moderately priced horizontal beam spectrophotometer. Three issues of specific concern are:

1. Unless the light beam of a photometer is perfectly collimated (meaning all rays are parallel), the beam enters and exits the sample as a cone of light. This deviation from perfect collimation means that the effective path length of light through the sample is longer than the actual physical dimension of the sample. The broader the cone angle, the longer the effective path length. Thus, the measured absorbance of a given sample will be higher when measured by a photometer with a broad cone of light than when measured using a highly collimated beam. It is typically true that plate readers have a broader cone of light than a spectrophotometer owing to their physical layout and the need to be able to read many samples quickly.
2. If the sample has an absorbance peak typical of organic dyes, e.g. 80 to 100 nm width, then the exact nature of the wavelength selection mechanism will determine the measured absorbance of the peak. Many plate readers use interference filters as a wavelength selection means. These filters have a bandpass many times that of the bandpass of a spectrophotometer. These filters also do not have the same degree of accuracy of the center wavelength of a good scanning spectrophotometer. The net result is that absorbance readings depend on the details of wavelength selection.
3. It is common to calibrate both plate readers and spectrophotometers using neutral density filters. These are sheets of glass that are tinted a neutral grey color, meaning that they absorb equally over a broad range of wavelengths. Their absorbance is measured in a spectrophotometer with results traceable to national standards, and then in the plate reader being tested. The degree of agreement between these readings is then used as a measure of accuracy of the plate reader results. However, a calibration process that relies on neutral density filters gives little or no information about items such as: out of band transmission (light passing from the source through the wavelength selection mechanism and the sample to the detector but not in the desired wavelength range), wavelength selection accuracy, bandpass of the wavelength selection, or the shape of the transmission curve of the bandpass selection means. This means that exclusive reliance on calibration using neutral density filters can lead to substantial disagreement (several percent) between different plate readers, even those of the same design, when they are measuring absorbances of spectral peaks.

The result of these differences in design is that a dye solution measured in a fixed path length cuvette in a horizontal beam spectrophotometer will generally not have the same absorbance when measured in a vertical beam plate reader in an open microtiter plate. The discrepancy will often be several percent, and can be much larger.

Thus, one aspect of the present invention takes into account a correction factor between absorbance measurements obtained in a user's spectrophotometer or plate reader, and in the manufacturer's or reference spectrophotometer. This aspect provides a method of correlation to accurately determine how the photometric readings made by the plate reader will relate to those made by the reference spectrophotometer used to characterize the reagents. Once this correlation is made, a correction is applied to the readings from the plate reader.

In one embodiment, a method of determining the correlation or correction factor includes the use of a special calibration plate, which is read in the reference spectrophotometer as well as in the plate reader. The calibration plate can comprise a series of sample holders, such as fixed-path length cuvettes containing different admixtures of the same solutions provided in the reagent kit, i.e. the sample solutions. These calibration materials have the same absorbance peak locations and widths utilized when the reagent kit is used to calibrate a liquid volume. Thus, the full capability of the plate reader (accuracy and bandwidth of the wavelength selection means, out of band transmission, collimation of the light beam, and linearity of response of the detection and electronic readout means) is tested. Any discrepancy between the plate reader and the reference spectrophotometer can be fully and reliably corrected.

Figure 4:
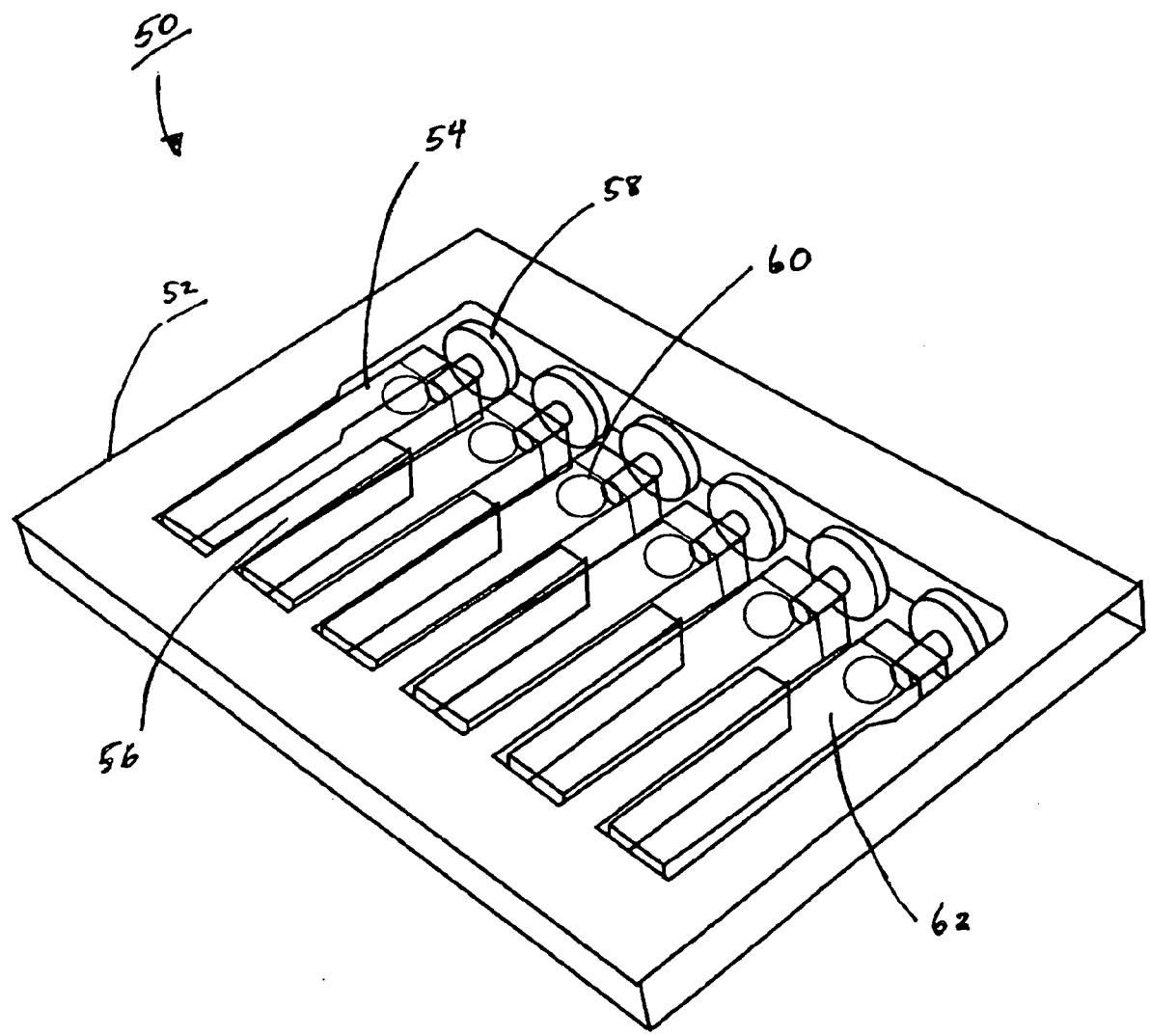
FIG. 4 is a schematic diagram of one embodiment of a calibration plate having a series of cells or cuvettes, similar to that illustrated in FIG. 1.

FIG. 4 is a schematic diagram of one embodiment of a calibration plate 50. Calibrator plate 50 includes a housing or casing 52 which holds a series of sample holders or cuvettes 54. Casing 52 includes spacers 56 for separating one cuvette from another. In this example, the sample holder 54 is the cuvette shown in FIG. 1, which provides a fixed path length l. Each cuvette has opposing parallel transparent side walls for allowing light to penetrate through the solution. Side wall 62 is parallel to another wall not shown here. Those of ordinary skill in the art can readily envisage other designs for the calibrator plate with a series of sample holders. Each sample holder 54 contains sample solutions having a first and second chromophore, as described previously. The solutions are sealed in sample holder 54 by cap 58 to prevent evaporation. Preferably, each well further includes an air bubble, to allow expansion of the sample solution. The cuvette is preferably designed to cause the bubble to move to an area not exposed to the electromagnetic radiation, i.e. an area adjacent cap 58.

More specifically, a glass or quartz material cell may be used with a Teflon stopper. When the cell is positioned horizontally the air bubble will remain adjacent the Teflon stopper for the following reasons. If the air bubble tries to leave the area adjacent the Teflon stopper, then one edge of the bubble will be in contact with the glass or quartz of the cell while the other edge will be in contact with the Teflon. The contact angle between the liquid-solid interface will be much smaller (less than 90°) at the glass-liquid interface than at the Teflon-liquid interface. The surface tension of the liquid will preferentially pull the air bubble back toward the Teflon, until both edges of the bubble are again in contact with the Teflon. Thus, the bubble appears to "stick" to the Teflon surface.

This embodiment of calibration plate 50 is designed to be readable by a vertical beam spectrophotometer, where the calibration plate is supported in a horizontal position as shown in FIG. 4. Alternatively, the calibrator plate can be designed to be readable by a horizontal beam spectrophotometer when supported in a vertical position.

In the calibration method, each sample is measured in a spectrophotometer of known accuracy (reference or manufacturer's spectrophotometer) where the reference spectrophotometer provides values traceable to national standards. These values may be recorded or encoded via a bar code that is printed and affixed to the calibration plate itself, or by other known methods. When a user begins the calibration process, the user first scans the barcode or otherwise transfers the information associated with the calibration plate into a computer for use by the calculation algorithm. The calibration plate is then read in the user's plate reader. The user's plate reader is thus calibrated against the reference spectrophotometer. In one embodiment, the solutions in the calibration plate can be liquids containing the same chromophores as used in the reagent kit described above. Thus, the plate reader can be calibrated to read exactly the same materials as it will measure in the subsequent steps of the liquid delivery calibration process.

In one embodiment, the calibrator plate comprises a first set of solutions of varying concentrations. This embodiment is exemplified by a calibrator plate with for example four different concentrations of calibration solutions. These solutions are labeled in the equations below with the subscript CAL.

The manufacturer measures the absorbance of, for example, a first calibrator solution, resulting in $A'_{CAL1}(n)$ and $A'_{CAL3}(n)$ at $\lambda_1$ and $\lambda_3$ respectively. The Beer-Lambert law rewritten for the first calibrator solution is:

$$A'_{CAL1}(1) = \epsilon'_{CAL1}(1) c'_{CAL1}(1) l_{CAL}(1) \text{ at } \lambda_1$$

$$A'_{CAL3}(1) = \epsilon'_{CAL3}(1) c'_{CAL3}(1) l_{CAL}(1) \text{ at } \lambda_3 \quad (11)$$

One of the calibrator vials is then filled with blank solution, and the resulting absorbances, $A'_{CAL1}(b)$ and $A'_{CAL3}(b)$, are employed in the Beer-Lambert equation:

$$A'_{CAL1}(b) = \epsilon'_{CAL1}(b) c'_{CAL1}(b) l_{CAL}(b) \quad (12)$$

$$A'_{CAL3}(b) = \epsilon'_{CAL3}(b) c'_{CAL3}(b) l_{CAL}(b) \quad (13)$$

When the user measures the first calibrator solution in the plate reader, the following relationships are obtained:

$$A_{CAL1}(1) = \epsilon_{CAL1}(1) c_{CAL1}(1) l_{CAL}(1) \text{ at } \lambda_1$$

$$A_{CAL3}(1) = \epsilon_{CAL3}(1) c_{CAL3}(1) l_{CAL}(1) \text{ at } \lambda_3 \quad (14)$$

A ratio of the readings at the two wavelengths in the two instruments of the first calibrator solution is:

$$CALR(1) \equiv \frac{\epsilon'_{CAL1}(1) c'_{CAL1}(1)}{\epsilon'_{CAL3}(1) c'_{CAL3}(1)} \frac{\epsilon_{CAL3}(1) c_{CAL3}(1)}{\epsilon_{CAL1}(1) c_{CAL1}(1)} \quad (15)$$

$$CALR(1) = \frac{A'_{CAL1}(1)}{A'_{CAL3}(1)} \frac{A_{CAL3}(1)}{A_{CAL1}(1)} \quad (16)$$

This ratio expresses how the user's plate reader reads a given calibrator solution vs. how the manufacturer's or reference spectrophotometer reads the calibrator solution. Four ratios will be obtained for each of the four different calibrator solutions, labeled as CALR(1), CALR(2), etc. If these CALR values are plotted against absorbance as measured in the plate reader at $\lambda_1$, a straight line results. Thus, for any given absorbance at $\lambda_1$, the correct CALR to use can be obtained by finding a linear regression. In other embodiments, a different number (more or fewer) of calibrator solutions may be used.

The readings of the blank filled calibrator are $A_{CAL1}(b)$ and $A_{CAL3}(b)$, providing the following relationships:

$$A_{CAL1}(b) = \epsilon_{CAL1}(b) c_{CAL1}(b) l_{CAL}(b) \quad (17)$$

$$A_{CAL3}(b) = \epsilon_{CAL3}(b) c_{CAL3}(b) l_{CAL}(b) \quad (18)$$

where $l_{CAL}(b)$ is the path length of the cuvette used for the blank filled calibrator.

A ratio of the blank calibrator readings obtained at $\lambda_3$ in the two systems is shown in eq. (19):

$$CALR_3(b) \equiv A'_{CAL3}(b) / A_{CAL3}(b) \quad (19)$$

The user then measures the calibrator plate at $\lambda_1$ and $\lambda_3$ with the plate reader, where the absorbance values are given by:

$$A_1 = \left( \epsilon_{Bl} c_B \frac{V_S}{V_T} + \epsilon_{bl} c_b \right) l \quad (20)$$

and $$A_3 = \epsilon_{b3} c_b l \quad (21)$$

where l is the path length in the well being measured, $V_S$ is the volume of sample, and $V_T$ is the total volume (sample plus blank) of liquid in the well.

Solving equation (21) for l provides:

$$l = \frac{A_3}{\epsilon_{b3} c_b} \quad (22)$$

To obtain an explicit value for l, a compensation must be made between the different readings of the reference spectrophotometer and the plate reader. This compensation can be obtained from the calibration ratio of eq. 19. Using that, and the result of the characterization of the blank of eq. (4), $$l = l' CALR_3(b) \frac{A_3}{A'_{b3}} \quad (23)$$

l will be different (potentially) for each well, depending on how much liquid was actually dispensed into that well.

The total volume of liquid in each well is calculated, based on the measured path length l as given by equation (22) and the geometry of the wells. Here the wells are truncated cones with diameter $\phi$ and half angle $\gamma$. The total volume $V_T$ in a given well filled to a depth of l is given by:

$$V_T = \pi l \frac{\phi^2}{4} + \pi \phi l^2 \frac{\tan(\gamma)}{2} + \pi l^3 \frac{\tan^2(\gamma)}{3} \quad (24)$$

The volume $V_S$ of sample added to each well is then, starting with equation (20) and solving for $V_S$:

$$A_1 - \epsilon_{bl} c_b l = \epsilon_{Bl} c_B \frac{V_S}{V_T} l \quad (25)$$

-continued $$V_S = V_T \left( \frac{A_1 - \varepsilon_{b1} c_b l}{\varepsilon_{B1} c_B l} \right) \quad (26)$$

Using equation (21) to eliminate l provides:

$$V_S = V_T \left( \frac{A_1 - A_3 \frac{\varepsilon_{b1} c_b}{\varepsilon_{b3} c_b}}{A_3 \frac{\varepsilon_{B1} c_B}{\varepsilon_{b3} c_b}} \right) \quad (27)$$

Dividing the terms in the parenthesis of eq. (27) by $A_3$ and applying the reagent concentration ratio $RCR'_B$ (eq. 7) generates the following relation:

$$V_S = \frac{V_T}{RCR_B} \left( \frac{A_1}{A_3} - \frac{\varepsilon_{b1} c_b}{\varepsilon_{b3} c_b} \right) = \frac{V_T}{RCR_B} \left( \frac{A_1}{A_3} - \frac{A_{CAL1}(b)}{A_{CAL3}(b)} \right) \quad (28)$$

So far in this equation, all absorbances refer to measurements that were made with the user's plate reader. In the case of the reagent concentration ratio, there is no data measured by the plate reader. The CALR value previously measured can be used however, to convert the reference spectrophotometer generated data to data that the user's plate reader would have read if it had been used to measure an RCR.

$$RCR(\text{corrected}) = RCR'_B/CALR \quad (29)$$

The resulting unknown sample volume is represented by the eq. (30):

$$V_S = \frac{V_T CALR}{RCR'_B} \left( \frac{A_1}{A_3} - \frac{A_{CAL1}(b)}{A_{CAL3}(b)} \right) \quad (30)$$

CALR is a function of the absorbance $A_1$ at $\lambda_1$ as measured in the plate reader. $RCR_B$ is a function of the Dilution Ratio (in this case $RD_B = V_S/V_T$) as given in equation (9). Thus, $V_S$ cannot be directly calculated because the value of $RCR_B$ is needed, which itself is dependent on $V_S$. Successive approximations can be used to calculate $V_S$. To obtain a preliminary value for $RCR_B$, the assumed value of $V_S$ (what the pipette is marked, or an estimated value) is divided by the total volume $V_T$ as an initial guess value of $RD_B$ in equation (9). Using this estimate of $RCR_B$, a calculation of $V_S$ is performed with equation (30). The new value of $V_S$ obtained is then used to refine the estimate of $RD_B$, and the new value of $RD'_B$ used to calculate a new value of $RCR_B$, which in turn is used to refine the value of $V_S$.

EXAMPLE

This example provides compositions of a reference solution and sample solutions, which can be diluted as necessary to obtain accurate absorbance measurements.

Blank solution. The blank solution is prepared by dissolving 4.564 g (grams) copper chloride dehydrate, 15.186 g EDTA (ethylenediaminetetraacetic acid, tetrasodium salt), a chelator for copper, and 6.953 g potassium hydrogen phthalate in 4 L (liters) of preserved diluent. Heat is applied only if necessary. The pH is tested and adjusted to 6.0±0.1 using 1N (normal) NaOH (approximately 21 mL). The resulting solution is filtered through a 0.45 micron filter into a tightly-capped glass bottle.

The specific gravity of the blank solution is measured by using pynknometer. The absorbance is measured in a reference spectrophotometer (Varian) using a 1 cm cuvette; the cuvette (or at least an inner wall portion, e.g., coating) is made of polystyrene. The reference spectrophotometer is set to zero with 0.02 M (molar) buffer in the cuvette. A scan 400–800 nm with 1 nm slit width and 0.2 sec (seconds) per reading is performed. A maximum absorbance peak should be observed at approximately 730 nm. A scan of 700–750 nm is then taken with a 0.2 nm slit width and 1 sec per reading. The slit is then set to 4 nm and read time is set to 5 seconds. The absorbance is measured at 520 and 730 nm.

The absorbance should be 0.610 in a 1 cm cuvette, within 0.003. If a batch measures too high, deionized water is added to reduce the absorbance to within the target range. If a batch measures too low, small amounts of the blank solution are added (no more than a few percent by volume) to come within the target range.

Range C solution. The target absorbance of this solution at 520 nm is 75 in a 1 cm pathlength cell. 1.888 g Amaranth is dissolved in 1000 g of the blank solution prepared above and the resulting solution is filtered through a 0.47 micron filter and stored in a tightly-capped brown glass jar in the dark.

1 g of the Range C solution is diluted with 30 g of the blank solution. This solution is weighed on a 4 place balance and exact weights are recorded. Care is taken to minimize vibration, draft, static electricity, and evaporation during this weighing process. Several glass vials are filled with the diluted solution. These solutions are capped and allowed to equilibrate in the sample compartment of the reference spectrophotometer (Varian). The temperature of the solution is recorded. The reference spectrophotometer is zeroed with 0.02 M buffer. A scan from 400 nm to 800 nm is taken by using 1 nm SBW (split bandwidth) and 0.2 second read time. Absorbances should be noted at 520 and 730 nm. The absorbances at 520 and 730 nm are then measured by using Advanced Reads, 4 nm SBW and 5 sec read time.

Range B solution. The target absorbance at 520 nm is 17.86 in a 1 cm pathlength cell. 312.5 g of the Range C solution, prepared as discussed above, is added to 1000 g of the blank solution. The resulting solution is mixed and filtered through a 0.47 micron filter and stored in a tightly-capped brown glass jar in the dark.

5 g of the Range B solution is diluted with 30 g of the blank solution. This solution is weighed on a 4 place balance and exact weights are recorded under the conditions described above. Several glass vials are filled with the diluted solution. These vials are capped and the solutions are allowed to equilibrate in the sample compartment of the Varian. The temperature of the solution is recorded. The Varian is zeroed with a 0.02 M buffer. A scan from 400 nm to 800 nm is taken by using 1 nm SBW and 0.2 second read time. Absorbances are noted at 520 and 730 nm. The absorbances at 520 and 730 mm are then measured by using Advanced Reads, 4 nm SBW and 5 sec read time.

These and other embodiments of the invention are included within the scope of the following claims.

What is claimed is:

1. A method of determining a volume comprising:
providing at least one sample including a first chromophore having an absorbance maximum at a first wavelength and a second chromophore having an absorbance maximum at a second wavelength;
exposing the at least one sample to electromagnetic radiation;

measuring an absorbance of the electromagnetic radiation by each chromophore;

exposing a blank to electromagnetic radiation, the blank being free of the first chromophore and including the second chromophore in a concentration equal to that in the at least one sample;

measuring an absorbance of the blank; and determining the volume of the at least one sample from the measured absorbance of the at least one sample and the measured absorbance of the blank.

2. The method of claim 1, wherein the volume is determined from the measured absorbance of the at least one sample, the measured absorbance of the blank, and a correction factor, wherein the correction factor is obtained by:

calculating a volume of the at least one sample based on the weight of the at least one sample, and comparing the volume calculated from the weight of the at least one sample with the volume determined from the measured absorbances.

3. The method of claim 1, further comprising the step of adding a diluent to the at least one sample.

4. The method of claim 3, further comprising the step of diluting with the diluent a concentration of the at least one sample appropriate for the volume to be determined.

5. The method of claim 4, wherein the diluent includes the same components as contained in the blank.

6. The method of claim 4, wherein the at least one sample to be diluted and the diluent are contained in a well and have a total volume denoted $V_T$, determined by:

$$V_T = \pi l \frac{\Phi^2}{4} + \pi \Phi l^2 \frac{\tan(\gamma)}{2} + \pi l^3 \frac{\tan^2(\gamma)}{3}$$

wherein $l$ refers to a path length of the sample in the well, $\Phi$ refers to the diameter of the well at the bottom, and $\gamma$ refers to the half angle of the well.

7. The method of claim 6, wherein the path length of the sample in the well, l, is determined by:

$$l = \frac{A}{\varepsilon_b c_b}$$

wherein the subscript "b" refers to the blank, A refers to the absorbance, $\varepsilon$ refers to the molar absorptivity, and c refers to the concentration.

8. The method of claim 1, wherein at least two samples are provided, each sample having a unique concentration of the first chromophore, and wherein the at least two samples are provided in a multi-well plate.

9. The method of claim 8, further comprising measuring at least one dimension of each well in the multi-well plate.

10. The method of claim 9, wherein the measured at least one dimension is traceable to national standards.

11. The method of claim 9, wherein the volume of each of the at least two samples is determined from the measured absorbance of each of the at least two samples, the measured absorbance of the blank, and the at least one dimension.

12. The method of claim 9, wherein the at least one dimension is measured to a level of error of no more than about 0.5%.

13. The method of claim 9, wherein the at least one dimension is the diameter measured at the bottom of the well.

14. The method of claim 9, wherein the at least one dimension is the half angle of the well.

15. The method of claim 1, wherein the volume of the at least one sample is denoted $V_S$, and is determined by:

$$V_s = V_T \left( \frac{A_1 - A_2 \frac{\varepsilon_{b1} c_b}{\varepsilon_{b2} c_b}}{A_2 \frac{\varepsilon_{B1} c_B}{\varepsilon_{b2} c_b}} \right)$$

wherein the subscripts 1 and 2 refer to the first and second chromophore, respectively, the subscript "B" refers to the sample, the subscript "b" refers to the blank, A refers to the absorbance, $\varepsilon$ refers to the molar absorptivity, c refers to the concentration, and $V_T$ refers to the sum of the sample volume plus blank volume.

16. The method of claim 1, wherein the volume of the at least one sample, $V_S$, is determined by:

$$V_s = \frac{V_T CALR}{RCR_B} \left( \frac{A_1}{A_2} - \frac{A_{b1}}{A_{b2}} \right)$$

wherein the subscripts 1 and 2 refer to the first and second chromophore, respectively, the subscript "B" refers to the at least one sample, the subscript "b" refers to the blank, the prime (') refers to a first spectrophotometer, $V_T$ refers to the sum of the sample volume plus blank volume, A refers to the absorbance, CALR refers to a calibration ratio of the absorbance values of the first and second chromophores, and RCR refers to a reagent concentration ratio.

17. The method of claim 1, wherein the volume determined is traceable to national standards.

18. The method of claim 1, further comprising the step of selecting as either or both of the first chromophore and the second chromophore a chromophore exhibiting a reduced temperature dependence of absorbance.

19. The method of claim 1, further comprising the steps of:

a. determining a temperature dependence of absorbance for the first chromophore and for the second chromophore;

b. measureing the temperatures of the first chromophore and the second chromophore at about the time of measuring the absorbances of each chromophore;

c. calculating a correction factor for each of the first chromophore and the second chromophore based on the determined temperature dependence of absorbance and measured temperatures of each; and d. using the calculated correction factor for the first chromophore and for the second chromophore in the step of determining the volume of the at least one sample.

20. A kit comprising:

a multi-well plate, for containing a plurality of samples and for exposing them to the electromagnetic radiation;

a plurality of samples, each sample including a first chromophore having an absorbance maximum at a first wavelength and a second chromophore having an absorbance maximum at a second wavelength, wherein each sample has a unique concentration of the first chromophore; and a blank free of the first chromophore and including the second chromophore in a concentration equal to that in each of the plurality of samples.

21. The kit according to claim 20, further comprising:
a calibration plate for calibrating a first spectrophotometer with a second spectrophotometer, the calibration plate having multiple cells containing a set of calibration solutions.

22. The kit of claim 20, wherein each of the samples has the same concentration of the second chromophore.

23. The kit of claim 20, further comprising a diluent for adding to at least one of the samples.

24. The kit of claim 23, wherein the diluent is free of the first chromophore and includes the second chromophore in a concentration equal to that in the at least one sample.

25. The kit of claim 23, further comprising instructions for diluting the at least one of the samples with the diluent.

26. The kit of claim 20, wherein either or both of the first chromophore and the second chromophore is a chromophore exhibiting a reduced temperature dependence of absorbance.

27. The kit of claim 20, further comprising instructions for:

a. determinging a temperature dependence of absorbance for the first chromophore and for the second chromophore;
b. measuring the temperatures of the first chromophore and the second chromophore at about the time of measuring the absorbances of each chromophore;
c. calculating a correction factor for each of the first chromophore and the second chromophore based on the determined temperature dependence of absorbance and measured temperatures of each;
d. measuring an absorbance of each chromophore in each of the plurality of samples; and
e. determining the volume of each of the plurality of samples using the absorbance measurements and the calculated correction factor for the first chromophore and for the second chromophore.

* * * * *